United States Patent [19]

Konomura

[11] Patent Number: 4,561,428
[45] Date of Patent: Dec. 31, 1985

[54] SUCTION CONTROLLER OF ENDOSCOPES

[75] Inventor: Yutaka Konomura, Hachioji, Japan

[73] Assignee: Olympus Optical Company Ltd., Japan

[21] Appl. No.: 630,071

[22] Filed: Jul. 12, 1984

[30] Foreign Application Priority Data

Jul. 18, 1983 [JP] Japan .................... 58-110227

[51] Int. Cl.$^4$ .............................................. A61B 1/00
[52] U.S. Cl. .......................................................... 128/4
[58] Field of Search .......................................... 128/4, 6

[56] References Cited

U.S. PATENT DOCUMENTS

| 3,958,566 | 5/1976 | Furihata | 128/4 |
| 4,412,531 | 11/1983 | Chikashige | 128/4 |
| 4,469,090 | 9/1984 | Konomura | 128/4 |

FOREIGN PATENT DOCUMENTS

| 56-9441 | 3/1981 | Japan. |
| 57-103619 | 6/1982 | Japan. |
| 57-103620 | 6/1982 | Japan. |

Primary Examiner—William H. Grieb
Attorney, Agent, or Firm—Ostrolenk, Faber, Gerb & Soffen

[57] ABSTRACT

A suction controller of an endoscope is provided with a valve member made of resilient material on a shiftable tube which is guided by a guide tube disposed within a support tube so that when liquid is fed said valve member is pressed against a valve seat disposed on said support tube with said shiftable tube shifted to break the communication between a suction tube and a channel of the endoscope. As a result, the liquid is no longer drawn into the suction tube during the liquid feeding and the shifting of the shiftable tube is guided by the guide tube, so that the reliable functions of the suction controller can be assured.

10 Claims, 8 Drawing Figures

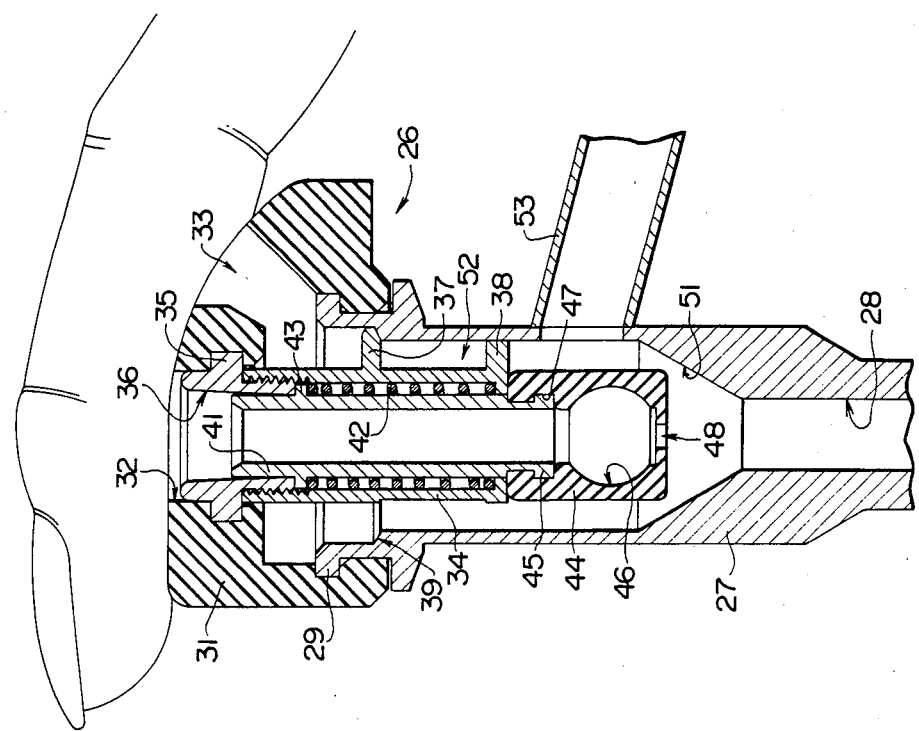
F I G. 4
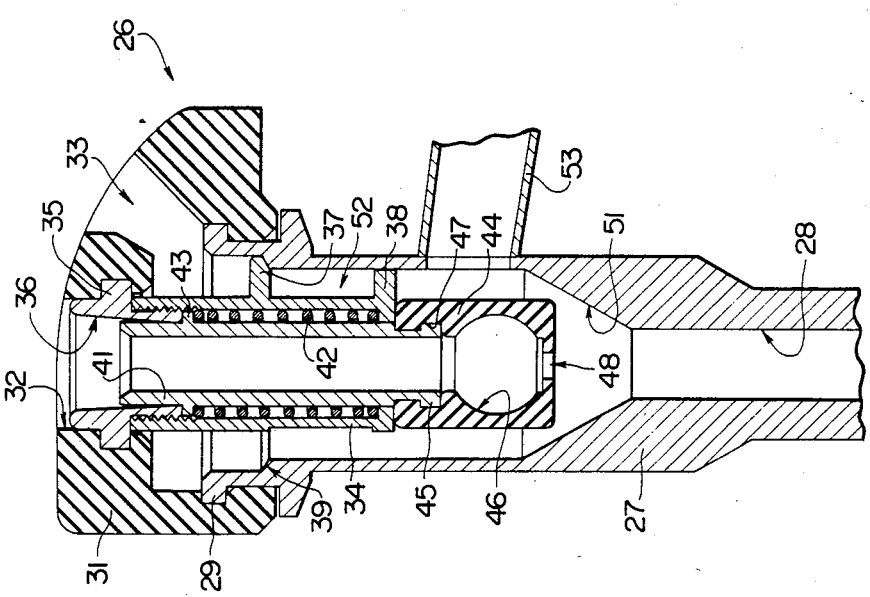
F I G. 3

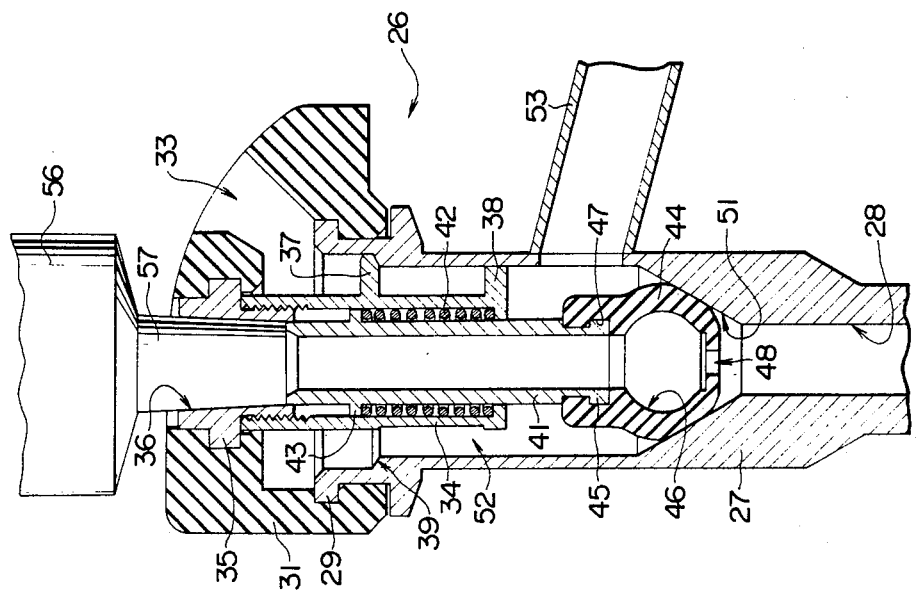
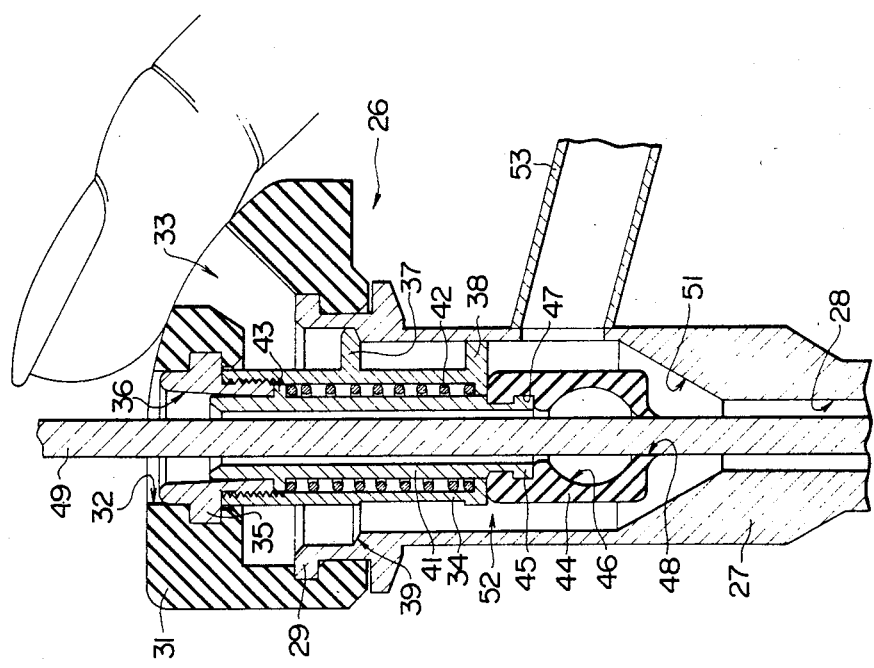

SUCTION CONTROLLER OF ENDOSCOPES

BACKGROUND OF THE INVENTION

The present invention relates to improvements in a suction controller for an endoscope which is capable of performing an air supply, water supply or a procedure for inserting operation instruments such as forceps in addition to a suction procedure by way of a channel of the endoscope.

Such a suction controller has been heretofore constructed as shown in FIG. 1. Specifically, a guide tube 5 comprises a first lower tube 3 and a second lower tube 4 both of which are threadedly connected to each other end to end. The guide tube 5 is disposed within an outer tube 1 in such a manner that a space portion 6 is formed between the guide tube 5 and the outer tube 1. A suction tube 2 is connected to the peripheral wall of the outer tube 1 whose lower end is connected to a channel of an endoscope. A slide tube 7 is inserted in the guide tube 5 and is resiliently held by a spring 8 which is interposed between the outer peripheral surface of the slide tube 7 and the inner peripheral surface of the guide tube 5. A support tube 10 is provided through a connecting tube 9 at the lower end of the slide tube 7. A slider 12 having a through-hole 11 through which an operation instrument passes is held by the support tube 10. A communicating hole 13 through which the space portion 6 communicates with the interior of the guide tube 5 is provided through the peripheral wall of the first tube 3. A cap 14 is mounted on the upper end of the outer tube 1. The cap 14 has a holding hole 15 through which the upper end of the guide tube 5 communicates with the exterior and an air hole 16 through which the space portion 6 communicates with the open air.

With the above-noted arrangement, suction of mucus or filth in a coeliac cavity can be effected by blocking the holding hole 15 and the air hole 16 with a finger. When both holes 15 and 16 are blocked, the suction path previously extending from air hole 16 to space portion 6 to the suction tube 2 is now changed to extend through the channel on the coeliac cavity as shown with an arrow a in FIG. 1, so that mucus or filth in the coeliac cavity can be drawn into the suction tube 2. An operation procedure using an operation instrument and a suction procedure can be simultaneously effected by inserting the operation instrument through the slide tube 7 and the through-hole 11 of the slider 12 into the channel and simultaneously blocking the air hole 16 with a finger. Furthermore, a liquid supply procedure can be effected by fitting the tip end of an injector into the slide tube 7 and slidingly pushing the slide tube 7 against the restoring force of the spring 8 to block the communicating hole 13 by the support tube 10 which shifts together with the slide tube 7. Accordingly, the interior of the guide tube 5 is shut off from the space portion 6 so that liquid can be fed from the injector through the channel into a coeliac cavity.

However, according to the conventional arrangement described above, since the support tube 10 which blocks the communicating hole 13 during the liquid supply procedure is slidingly fitted into the guide tube 5, it is impossible to seal the sliding plane of the support tube 10 in a reliable manner. Accordingly, a part of liquid ejected from an injector is drawn in the suction tube 2 through the space portion 6 and thus there is a possibility that the liquid may not be completely fed into a coeliac cavity.

SUMMARY OF THE INVENTION

In view of the foregoing, it is an object of the present invention to provide a suction controller for an endoscope which is capable of reliably blocking the path between a channel of the endoscope and a suction tube during a liquid supply procedure.

According to the present invention, a valve member formed of resilient material is provided on a shiftable tube which is guided by a guide tube and is pushed against a valve seat during a liquid supply procedure so as to block the path between the channel of the endoscope and the suction tube in a reliable manner. Accordingly, during the liquid supply procedure, liquid does not enter into the suction tube and the shiftable tube is guided by the guide tube, thereby, assuring reliable functions of the suction controller.

BRIEF DESCRIPTION OF THE DRAWINGS

FIG. 3 is an enlarged sectional view of an embodiment of a suction controller according to the present invention;

FIG. 4 is a sectional view illustrating the suction controller shown in FIG. 3 which is in a suction procedure;

FIG. 5 is a sectional view illustrating the suction controller shown in FIG. 3 which is in a procedure for inserting a forceps;

FIG. 6 is a sectional view illustrating the suction controller shown in FIG. 3 which is in a liquid supply procedure;

DESCRIPTION OF THE PREFERRED EMBODIMENTS

Figure 1:
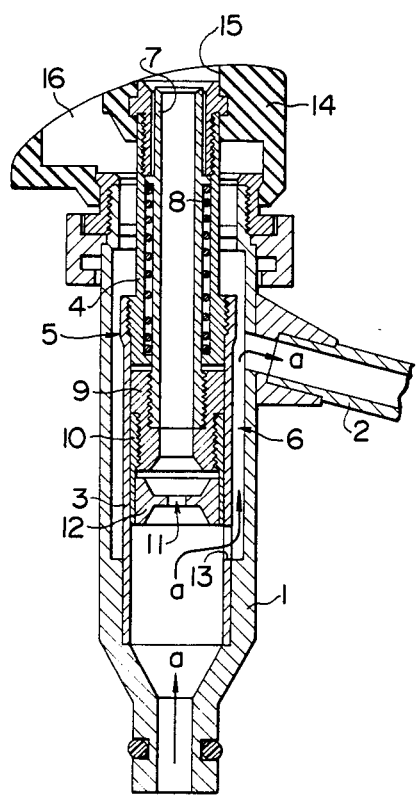
FIG. 1 is an enlarged sectional view illustrating an example of a conventional suction controller.
Figure 2:
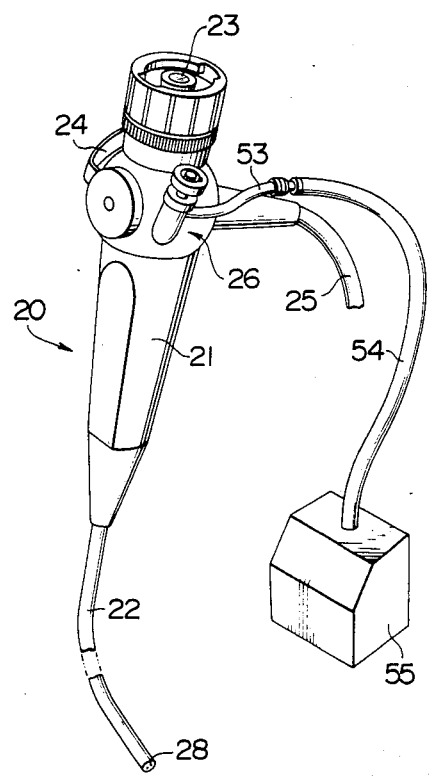
FIG. 2 is a perspective view of an endoscope provided with a suction controller according to the present invention.

Referring now to FIG. 2, an endoscope 20 comprises an operating portion 21 and an inserting portion 22. The operating portion 21 includes an eyepiece portion 23, an operating knob 24 for bending the distal end portion of the insertion portion 22, a light guide cable 25 which is connected to a light source (not shown) and a suction controller 26. Details of the arrangement of the suction controller 26 are shown in FIG. 3. The suction controller 26 has a support tube 27 which is secured to the operating portion 21. The support tube 27 communicates with a channel 28 of the endoscope. The channel 28 extends over an overall length of the operating portion 21 and the inserting portion 22. The front end (lower end in the figure) of the channel 28 opens at the distal end of the inserting portion 22 (see FIG. 2). A flange-shaped cap holder 29 is formed at the back end (upper end in the figure) of the support tube 27. (It is to be noted that the words "front (lower)" and "back (upper)" as used herein indicate the inserting portion side and the operating portion side of the endoscope, respectively.) A cap 31 which is formed of comparatively hard and resilient material such as fluorine rubber, silicone rubber, nitrile rubber (NBR) and urethane rubber is hermetically and detachably mounted on the cap holder 29. The cap 31 has a holding hole 32 and an air hole 33 which pass through the wall thereof. The holding hole 32 is located on an extension of the center axis of the support tube 27 and the air hole 33 is located out of the center axis of the support tube 27. A holding ring 35 to which the upper end of a guide tube 34 is threadedly secured is fitted and held in the holding hole 32. The holding ring 35 has a tapered plane 36 formed in the inner periphery thereof for fitting an injector, as will be described later. A plurality of first support pieces 37 and a plurality of second support pieces 38 are arranged respectively on the outer periphery of the guide tube 34 spacedly in its axial direction and along the peripheral direction of the guide tube 34. The first support 37 engages a step which is formed on the inner periphery of the back end portion of the support tube 27 so that the support tube 27 is not further pushed back. The second support piece 38 prevents swing of the guide tube 34 in abutment with the inner peripheral surface of the intermediate portion of the support tube 27.

A slide tube 41 is slidably fitted in the guide tube 34 as a shiftable tube and is resiliently urged backwardly by a spring 42 which is interposed between the outer peripheral surface of the slide tube 41 and the inner peripheral surface of the guide tube 34. Normally, slide tube 41 is located in the position as shown in FIG. 3, wherein a collar 43 projectedly provided on the outer periphery of the slide tube 41 abuts against the holding ring 35. In addition, under the normal condition, the front end portion of the slide tube 41 projects forwardly in the longitudinal direction from the guide tube 34. Also, a valve member fixing portion 45 on which a valve member 44 is mounted is formed on the outer periphery of the projected front end portion of the slide tube 41. The valve member 44 is a substantially pillar-shaped member made of resilient material such as fluorine rubber, silicone rubber, NBR and urethane rubber in which a spherical hollow portion 46 is formed, and has an opening 47 at the upper end thereof which is attached to the valve member fixing portion 45. A comparatively small through-hole 48 is formed on the front end of the valve member 44 so as to allow an operation instrument such as a forceps 49, to pass therethrough closely (see FIG. 5).

The valve member 44 under the normal condition shown in FIG. 3 faces a valve seat 51 apart therefrom, which seat is formed in a tapered form on the inner wall of the support tube 27. When the slide tube 41 is pushed down, the valve member 44 bears against the valve seat 51 so that the path between a space portion 52 formed between the outer peripheral surface of the guide tube 34 and the inner peripheral surface of the support tube 27 and the channel 28 is blocked (see FIG. 6). A suction tube 53 has its one end connected to the side wall of the support tube 27 and communicates with the space portion 52. The other end of the suction tube 53 is connected through a flexible tube 54 to a suction apparatus 55, as shown in FIG. 2.

In operation, when the suction apparatus 55 is operated under the normal condition shown in FIG. 3, the suction force is exerted through the flexible tube 54 and the suction tube 53 on the space portion 52. At this time, since the air hole 33 is open to the atmosphere, air is drawn through the air hole 33 into the space portion 52 and accordingly the suction force is not exerted through the channel 28 on a coeliac cavity.

When mucus or filth is to be drawn, both the holding hole 32 and the air hole 33 which have been open to the exterior are now blocked by covering the whole upper surface of the cap 31 with a finger, as shown in FIG. 4, whereby the communication between the space portion 52 and the exterior is broken and the suction force is exerted through the suction tube 53 on the channel 28. As a result, mucus or filth in the coeliac cavity is drawn from the channel 28 through the space portion 52 in the suction tube 53.

When a forceps 49 is to be used, it is inserted from the upper end opening of the slide tube 41 through the holding hole 32, as shown in FIG. 5, and is guided through the hollow portion 46 of the valve member 44 and the through-hole 48 to the channel 28. Under this condition, since the through-hole 48 becomes in air tightness with the forceps 49 closely fitted thereinto, there is no likelihood that the space portion 52 communicates through the slide tube 41 with the exterior. Further, since the suction tube 53 communicates through the space portion 52 and the air hole 33 with the atmosphere to draw air, there is no likelihood that the suction force is exerted on the channel 28.

When the suction procedure is effected while the forceps 49 is in use, the air hole 33 in the cap 31 is covered with a finger, as shown in FIG. 5, whereby the communication between the space portion 52 and the atmosphere is broken and mucus or filth in a coeliac cavity can be drawn accordingly by suction.

When liquid such as a liquid medicine is to be fed through the channel 28, a tapered tip end 57 of an injector 56 is fitted into the tapered inner peripheral surface 36 of the holding ring 35, as shown in FIG. 6. The slide tube 41 is slidingly pushed in against the resilient force of the spring 42 by applying a pushing force to the injector 56 to press the valve member 44 against the valve seat 51 with the result of resilient deformation of the valve member 44, whereby the communication between the space portion 52 and the channel 28 is broken and the space portion 52 communicates through the air hole 33 with the atmosphere to draw air. While this condition is maintained, the liquid is ejected by operating the injector 56. The liquid is not drawn in the suction tube 53 but is reliably fed through the channel 28 into the coeliac cavity.

Figure 7:
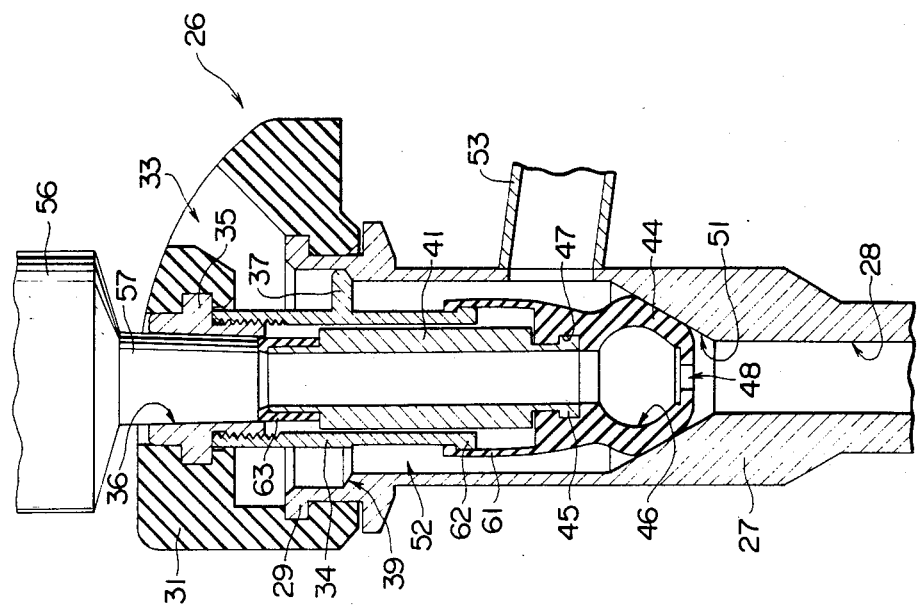
FIG. 7 is an enlarged sectional view illustrating another embodiment of a suction controller according to the present invention.
Figure 8:
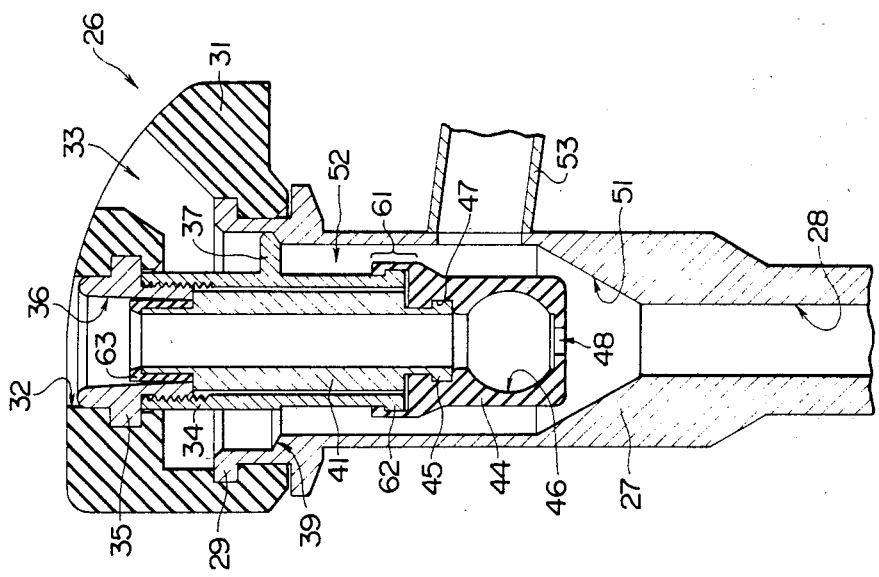
FIG. 8 is a sectional view illustrating the suction controller shown in FIG. 7 which is in a liquid supply procedure.

In FIG. 7, which illustrates a second embodiment of the present invention, a thin wall cylinder-shaped expandable portion 61 is connected with the valve member 44 in place of the spring 42 which urges the slide tube 41 in the first embodiment. Specifically, a lock 62 is formed on the lower end outer periphery of the guide tube 34 and the upper end of the expandable portion 61 is attached to the lock 62. This structure can be used in a manner similar to the first embodiment. When liquid such as a liquid medicine is to be injected with an injector 56, the tapered tip end 57 of the injector 56 is held by pushing it into the tapered inner peripheral surface 36 of the holding ring 35 and the expandable portion 61 is then stretched, as shown in FIG. 8. Thus, the same action as the spring 42 in the first embodiment is attained.

Furthermore, it is to be noted that in the second embodiment, a cylindrical packing 63 made of rubber is provided on the upper end of the slide tube 41 so that liquid tightness between the packing 63 and the tapered tip end 57 of the injector 56 can be secured by pressing the tapered tip end 57 against the packing 63.

What is claimed is:

1. A suction controller of an endoscope, comprising:
    a support tube communicating with a channel of said endoscope and having a valve seat on the inner periphery thereof;
    a suction tube connection to said support tube at a position located above said valve seat and normally communicating with said support tube;
    a guiding tube provided within said support tube;
    a shiftable tube which is slidably guided by said guide tube within said support tube and is movable between an upper and a lower position;
    actuation means for resiliently urging said shiftable tube upwardly into said upper position, and
    a resilient valve member mounted on said shiftable tube and having a through-hole through which said shiftable tube communicates with said channel, said valve member closely bearing against said valve seat to break the communications between said channel and said suction tube when said shiftable tube is moved into said lower position in response to the application of an external downward force applied to said shiftable tube, said shiftable tube together with said resilient valve member returning to said upper position under the focus of said actuation means alone when said externally applied downward force is removed from said shiftable tube.

2. A suction controller according to claim 1 in which said acutuation means is a spring member interposed between said guide tube and said shiftable tube.

3. A suction controller according to claim 1 in which said actuation means is formed of a stretchable portion which is integrally connected to said valve member and is mounted on said guide tube at one end thereof.

4. A suction controller according to claim 1 in which said shiftable tube is provided with a resilient member serving as a packing at the upper end thereof.

5. A suction controller according to claim 1 in which said resilient valve member is formed of resilient material such as any one of fluorine rubber, silicone rubber, nitryl rubber and urethane rubber.

6. A suction controller according to claim 1 in which said resilient valve member is composed of a substantially pillar-shaped member within which a spherical hollow portion is formed.

7. A suction controller according to claim 1 in which said resilient valve member has a through-hole through which a forceps may be passed.

8. A suction controller according to claim 1 wherein said shiftable tube includes a surface at the upper end thereof which is accessible externally of the endoscope and against which a liquid supply instrument may be placed in abutment to permit said instrument to apply a downward force to said shiftable tube and move said shiftable tube from said upper to said lower position.

9. A suction controller according to claim 1 further including an opening extending from a space in said support tube which communicates with said suction tube to the atmosphere.

10. A suction controller according to claim 1, wherein the shape of said resilient valve member in the undeformed condition is different than the shape of said valve seat and wherein said valve member is deformed and conforms to the shape of said valve seat when said shiftable tube is moved into said lower position.

* * * * *